United States Patent [19]

Bowman

[11] Patent Number: 4,463,261

[45] Date of Patent: Jul. 31, 1984

[54] ANALYSIS APPARATUS

[75] Inventor: George E. Bowman, Clophill, England

[73] Assignee: National Research Development Corporation, London, England

[21] Appl. No.: 365,390

[22] Filed: Apr. 5, 1982

[30] Foreign Application Priority Data

May 7, 1981 [GB] United Kingdom ............... 8113916

[51] Int. Cl.³ .............................................. G01J 1/00
[52] U.S. Cl. .................................... 250/339; 356/448
[58] Field of Search ................ 250/338, 339; 356/445, 356/448

[56] References Cited

U.S. PATENT DOCUMENTS 3,653,772  4/1972  Berge ................................... 356/448
4,171,918  10/1979 Mactaggart .......................... 250/339
4,260,262  4/1981  Webster .............................. 356/448

FOREIGN PATENT DOCUMENTS 960618   6/1964  United Kingdom .
1039746  8/1966  United Kingdom .
1332112  10/1973 United Kingdom .

Primary Examiner—Janice A. Howell
Attorney, Agent, or Firm—Cushman, Darby & Cushman

[57] ABSTRACT

For indication of the amount of a constituent in a substance, for example the proportion of moisture in hay, a pair of light-emitting diodes 1 and 2 have their emissions reflected from the substance being analyzed. The diodes emit radiation in narrow bands selected so that there is differential reflection depending on the proportion of the constituent in the substance. The supply currents to the diodes are switched in alternate sequence and their relative magnitudes adjusted to give minimum output at the switching frequency. For determining the proportion of moisture in hay suitable wavelengths are 1450 nm and 1300 nm. The diodes may be constructed as InGaAsP/InP diodes with the proportions of the constituents adjusted to give emission at the required wavelengths.

14 Claims, 2 Drawing Figures

ANALYSIS APPARATUS

This invention relates to analysis apparatus. It is concerned with apparatus for indicating the proportion of a particular constituent in a substance. It has application in indicating the proportion of moisture in grass cut in preparation for hay or silage.

In haymaking it is essential if the hay is to be successfully produced to store the grass when it has a moisture content within a fairly narrow range. Existing techniques of estimating or measuring the moisture content of grass are unreliable or unsatisfactory.

It is an object of the invention to provide analysis apparatus for indicating the proportion of a particular constituent in a substance, especially the moisture in cut grass.

According to the invention, analysis apparatus comprises two light-emitting diodes which emit narrow-band radiation of different wavelengths selected so that a sample containing a particular constituent differentially reflects radiation emitted from the diodes at the two wavelengths depending on the proportion of the constituent, radiation detection means positioned to receive radiation from the diodes after reflection from the sample, means for switching the electrical supply currents to the diodes in alternate sequence, and means for varying the ratio of the electrical supply currents to the diodes so as to minimise any signal component at the switching frequency in the output of the detector.

In carrying out the invention one or more additional diodes can be provided together with means for switching the supply currents to selected pairs of diodes in alternate sequence. The pairs of diodes are selected so that different constituents in the sample cause differential reflection at the radiation frequencies of the pair of diodes selected.

The wavelengths of the radiation emitted by the two light-emitting diodes are preferably in the range between 1000 nm and 2800 nm.

As applied to the indication of the proportion of moisture in grass for example, the apparatus takes advantage of the fact that at some wavelengths in the near infrared region the reflectance of grass varies markedly in proportion to its moisture content. This property is limited to certain narrow bands, one band being centred at 1440 nm with another centred at 1930 nm. At other wavelengths close to these values, for example at 1300 nm, the reflectance is little affected by moisture content. Thus the ratio in the magnitudes of the signals reflected at two appropriately selected wavelengths is a measure of the moisture content.

The apparatus also takes advantage of the fact that the output of a light emitting diode is a nearly linear function of its drive current and that, unlike filament lamps, the spectrum of the output remains substantially identical irrespective of changes in the drive current.

In order that the invention may be more fully understood reference will now be made to the accompanying drawings in which.

Figure 1:
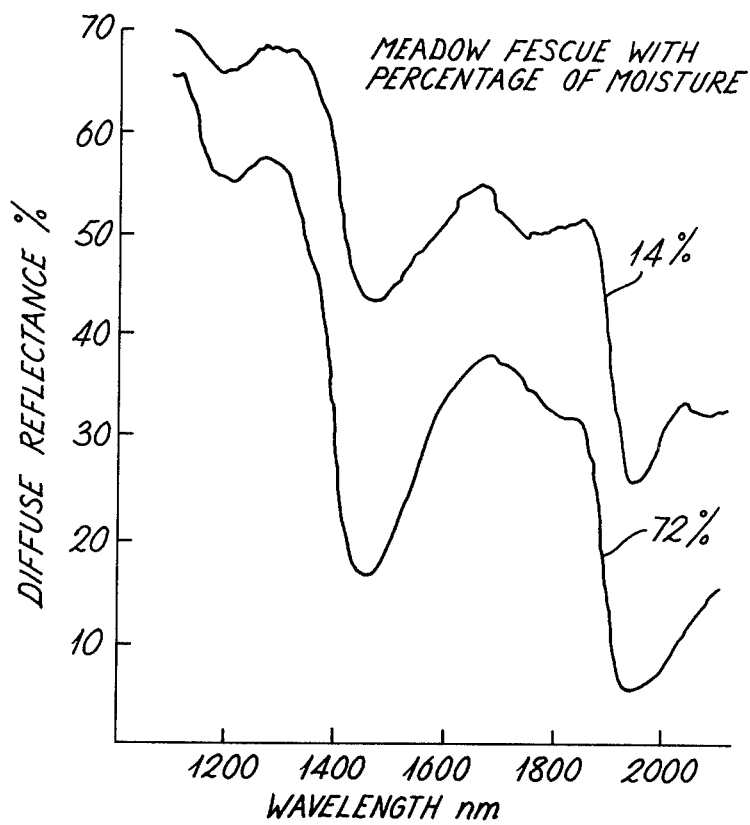
FIG. 1 is a curve showing the reflectance of a particular grass sample at different wavelengths and for two different values of moisture content.

Referring now to FIG. 1 there is illustrated therein the percentage reflectance from meadow fescue grass when radiated with infrared, of wavelengths from 1100 nm to over 2000 nm. The upper curve shows the reflectance of meadow fescue containing 14% moisture on a wet basis while the lower curve illustrates reflectance with 72% moisture. It will be seen that at say 1300 nm the effect of increasing the moisture causes little change in the reflectance. However, at 1450 nm and again at 1920 nm the effect of the moisture is to cause a very marked change in the reflectance.

This differential effect at two appropriately selected wavelengths is used in apparatus embodying the invention to provide an indication of the degree of moisture in grass cut for haymaking or silage making.

Figure 2:
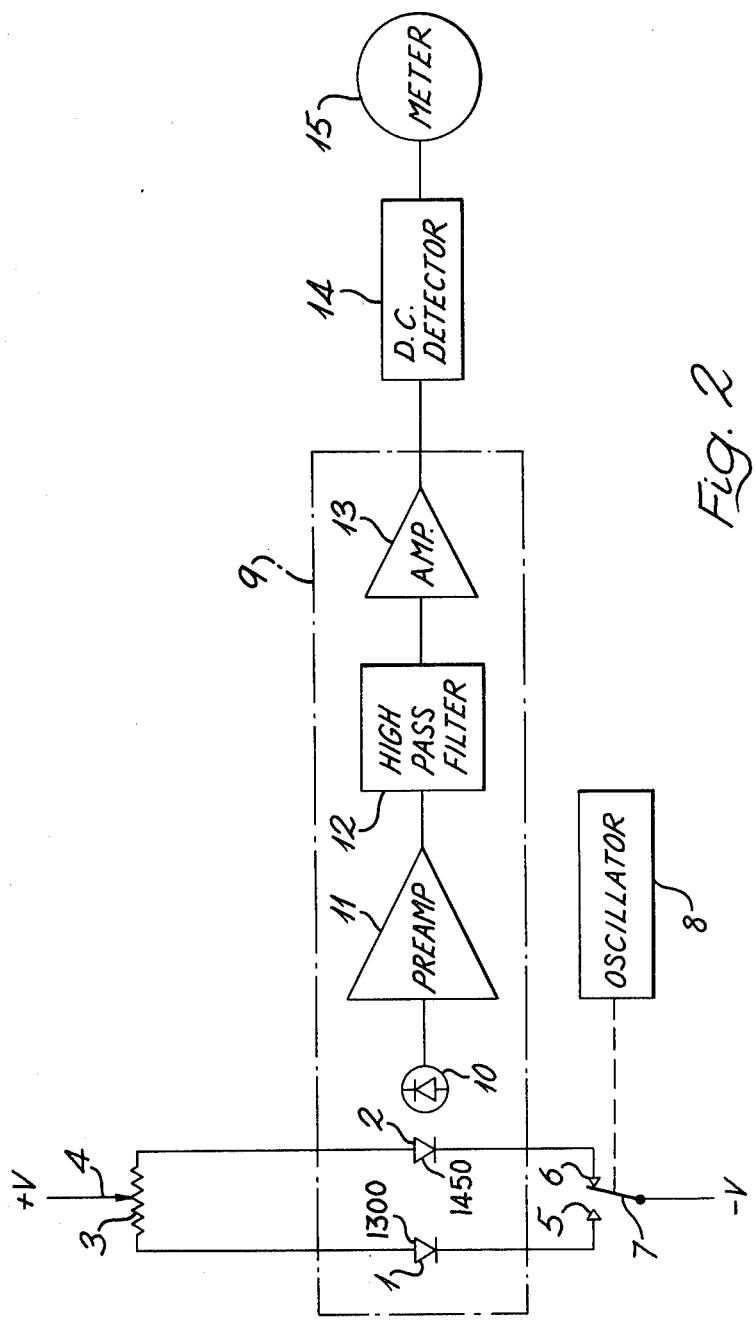
FIG. 2 is a block diagram of apparatus embodying the invention.

A block diagram of apparatus embodying the invention is shown in FIG. 2. Two radiation-emitting diodes 1 and 2 are provided. Diode 1 emits radiation of a wavelength of 1300 nm while diode 2 emits radiation at a wavelength of 1450 nm. The two diodes have one of their electrodes connected to opposite ends of a resistor 3 which is provided with a slider 4 connected to one terminal of a supply voltage V. The other electrodes of the two diodes 1 and 2 are connected to the two terminals 5 and 6 of a two-way switch, the switching member 7 of which is connected to the other terminal of supply V. Switch 7 is operated by an oscillator 8.

Diodes 1 and 2 are mounted in a head or probe 9 so that the radiation from them can be directed onto a sample, for example of hay or grass, the moisture content of which it is desired to measure. Radiation reflected from the sample is detected in photodetector 10 also mounted in head 9 and the output from photodetector 10 passes through a preamplifier 11 and high pass filter 12 to a further amplifier 13. Circuits 11, 12 and 13 are included in the head 9. The output from amplifier 13 is fed to a rectifier 14 and from thence to a meter 15.

In operation of the apparatus oscillator 8 operates switch 7 to cause lamps 1 and 2 to illuminate alternately. The relative magnitudes of the currents through the two lamps is determined by the position of slider 4 on resistor 3. Radiation reflected from the sample will be detected in photodetector 10 and high pass filter 12 passes only those components of the detected signal which are at or above the frequency of operation of oscillator 8. If the magnitudes of the radiation reflected from the samples are different at the two different wavelengths then the output of amplifier 13 will have an alternating component at the frequency of oscillator 8 and the magnitude of this component will be indicated in meter 15. Slider 4 is adjusted to reduce the magnitude of the a.c. component to zero and when this is indicated the magnitudes of the signals reflected from each lamp are equal. The position of slider 4 for this null indication is then a measure of the moisture content of the sample.

The accuracy of the result depends on the fact that the spectra of the outputs from diodes 1 and 2 do not appreciably vary for different values of current through the diodes. Thus as slider 4 is moved over resistor 3, although the magnitudes of the outputs from the two diodes vary, the wavelengths of their outputs do not. The apparatus also makes use of the feature that that the magnitude of the output from a diode is linearly related to the magnitude of the current through it. This enables the position of slider 4 on resistor 3 to be a direct indication of the relative magnitudes of the light emitted from the two diodes and hence resistor 3 can be linearly calibrated in terms of the moisture content of samples.

By utilising the output from detector 14 to control the magnitudes of the currents through diodes 1 and 2, the apparatus can be arranged to give an automatic indication of moisture content without the need for operator intervention. For this purpose the phase of the output from detector 14 needs to be indicated and this can be done by arranging for detector 14 to be of the phase-sensitive type with a reference signal fed to it from oscillator 8. It will be understood in practice that switch 7, although shown as a mechanical switch, will in practice be a solid state switching device. Similarly, although control of the currents through diodes 1 and 2 may be achieved by driving slider 4 or resistor 3 with a servo-motor, in practice entirely electronic means are preferable.

Instead of using probe 9 directly to shine onto a sample, the radiation from diodes 1 and 2 can be fed through light pipes or optical fibres to a reading head and similarly reflected radiation from a sample can be fed to photodetector 10 through optical fibres. The wavelengths of the outputs of diodes 1 and 2 can be determined by providing appropriately fabricated lamps. These diodes can be constructed from elements selected from group III and group V of the periodic table, so constituted that the emitted radiation lies in the range between 1000 nm and 2800 nm. For example diodes 1 and 2 can comprise InGaAsP/InP diodes with the proportion of the constituents in the InGaAsP layer adjusted to give the required emission wavelength. The following table gives the proportions by weight of Indium, Gallium, Arsenic and Phosphorus for the required wavelengths.

|    | 1300 | 1450 |
|----|------|------|
| In | 77   | 76   |
| Ga | 23   | 24   |
| As | 60   | 70   |
| P  | 40   | 30   |

The indication obtained from the apparatus described above can be utilised by an operator or else can provide an input signal to process control equipment.

The apparatus described and illustrated in FIG. 2 gives an indication of moisture content. Similar apparatus can be used for the measurement of other constituents in a sample such as oil, fat, protein or starch content. In each case pairs of lamps emitting on two appropriate wavelengths are required, with one wavelength chosen so that there is little variation in reflectance for wide variation in the content of the constituent and with the other wavelength chosen so that there is a large change in reflectance for different proportions of the constitutent.

For example, both water and starch absorb in the region of 1450 nm. Thus the moisture content of a sample which was being estimated on the basis of its reflectance ratio at 1450 nm and 1300 nm would be subject to error if a varying proportion of starch were present. But starch also absorbs strongly at 2100 nm, where water does not. Hence a third diode, constructed so as to emit at 2100 nm, can be used to correct the measurement reflectance at 1450 nm for the presence of starch in the sample.

I claim:

1. Analysis apparatus comprising two light-emitting diodes which emit narrow-band radiation of different wavelengths so that a sample containing a particular constituent differentially reflects radiation emitted from the diodes at the two wavelengths depending on the proportion of the constituent, radiation detection means positioned for receiving radiation from the diodes after reflection from the sample, means for switching the electrical supply currents to the diodes in alternate sequence, and means for varying the ratio of the electrical supply currents to the diodes so as to minimise any signal component at the switching frequency in the output of the radiation detecting means.

2. Apparatus as claimed in claim 1 in which one or more additional diodes are provided together with means for switching the electrical supply currents to selected pairs of diodes in alternate sequence.

3. Apparatus as claimed in claim 1 in which the wavelengths of the radiation emitted by the said two light emitting diodes are in the range of between 1000 nm and 2800 nm.

4. Apparatus as claimed in claim 3 in which the wavelengths of the radiation emitted by the said two light emitting diodes are 1300 nm and 1450 nm.

5. Apparatus as claimed in claim 1 in which the diodes are constructed from elements selected from group III and group V of the periodic table.

6. Apparatus as claimed in claim 5 in which the diodes are InGaAsP/InP diodes.

7. The apparatus as claimed in any one of the preceding claims in which the means for varying the ratio of the electrical supply currents to the diodes comprises a potentiometer the opposite ends of which are connected to the diodes and the slider terminal of which is connected to an electrical supply terminal.

8. Apparatus as claimed in claim 7 further including means for detecting components at the switching frequency in the output of the radiation detecting means and automatically adjusting the position of the slider to minimise such components.

9. An apparatus for analyzing the amount of a predetermined constituent contained by a sample, comprising:
   first radiation source means, responsive to a first current, for emitting a first radiation of a first predetermined wavelength for reflection by said sample, the intensity of said first radiation being linearly related to the magnitude of said first current;
   second radiation source means, responsive to a second current, for emitting a second radiation of a second predetermined wavelength different from said first predetermined wavelength for reflection by said sample, the intensity of said second radiation being linearly related to the magnitude of said second current;
   current supply means for alternately applying said first current to said first radiation source means and said second current to said second radiation source means, said alternation occurring at a predetermined frequency;
   radiation detecting means for producing a first signal indicating the intensity of the radiation produced by said first and second radiation source means reflected by said sample; and
   current ratio control means for controlling the ratio of said first and second currents to minimize the variation in said first signal caused by the difference in the reflectance by said sample of said first and second wavelengths.

10. An apparatus as in claim 9 wherein
said constituent absorbs said first radiation to a different degree than said constituent absorbs said second radiation.

11. An apparatus as in claim 10 wherein:

said constituent is water;
said first predetermined wavelength is 1300 nm; and
said second predetermined wavelength is 1450 nm.

12. An apparatus as in claim 9 wherein:
said current ratio control means includes a potentiometer, manually adjustable by a user, having a graduated scale directly indicating said amount of predetermined constituent contained by said sample; and
said apparatus further comprises indicating means for indicating when said variation in said first signal is at a minimum.

13. An apparatus as in claim 9 wherein said radiation detecting means includes:

photodetector means for producing a second signal indicating the intensity of said first and second radiations reflected by said sample; and
electrical high-pass filter means, responsive to said second signal, for producing said first signal, said first signal comprising only those frequency components of said second signal which are at or above said predetermined frequency of said alternation of said current supply means.

14. An apparatus as in claim 9 wherein:
said apparatus further comprises a probe; and
said first and second radiation source means and said radiation detecting means are fixedly attached adjacent to one another within said probe.

* * * * *